United States Patent
Ostrow

(10) Patent No.: US 7,532,927 B1
(45) Date of Patent: May 12, 2009

(54) IMPLANTABLE MEDICAL DEVICE AND ASSOCIATED METHOD FOR REDUCING AN AFFECT OF A VIBRATORY ALERT ON A VIBRATION-SENSITIVE SENSOR

(75) Inventor: Eliot L. Ostrow, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 96 days.

(21) Appl. No.: 11/458,536

(22) Filed: Jul. 19, 2006

(51) Int. Cl.
*A61N 1/08* (2006.01)

(52) U.S. Cl. .............................. 607/3; 607/36; 600/552

(58) Field of Classification Search ................ 381/71.2, 381/71.7, 71.13, 71.17; 600/25, 481, 515, 600/547; 607/17, 19, 23, 9
See application file for complete search history.

(56) References Cited

U.S. PATENT DOCUMENTS

| | | | |
|---|---|---|---|
| 4,490,841 A * | 12/1984 | Chaplin et al. ............ | 381/71.14 |
| 5,179,947 A * | 1/1993 | Meyerson et al. ............. | 607/19 |
| 6,002,963 A | 12/1999 | Mouchawar et al. | |
| 6,527,729 B1 | 3/2003 | Turcott | |
| 6,609,023 B1 * | 8/2003 | Fischell et al. .............. | 600/515 |
| 6,622,041 B2 * | 9/2003 | Terry et al. .................... | 607/9 |
| 6,942,622 B1 | 9/2005 | Turcott | |
| 6,994,676 B2 * | 2/2006 | Mulligan et al. ............ | 600/508 |
| 7,272,443 B2 * | 9/2007 | Min et al. ..................... | 607/17 |
| 2004/0057584 A1 * | 3/2004 | Kakuhari et al. ........... | 381/71.2 |
| 2005/0101831 A1 * | 5/2005 | Miller et al. .................. | 600/25 |
| 2005/0113705 A1 * | 5/2005 | Fischell et al. .............. | 600/515 |
| 2006/0224204 A1 * | 10/2006 | Hettrick et al. ............... | 607/23 |

FOREIGN PATENT DOCUMENTS

WO      2005048647      5/2005

* cited by examiner

*Primary Examiner*—Carl H Layno
*Assistant Examiner*—Luther G Behringer
(74) *Attorney, Agent, or Firm*—Steven M. Mitchell

(57) ABSTRACT

An implantable medical device and associated method are provided including a vibratory alert and a vibration-sensitive sensor. Further included is a circuit in communication with the vibratory alert and the vibration-sensitive sensor. Such circuit is adapted for at least reducing an affect of the vibratory alert on the vibration-sensitive sensor.

26 Claims, 4 Drawing Sheets

US 7,532,927 B1

IMPLANTABLE MEDICAL DEVICE AND ASSOCIATED METHOD FOR REDUCING AN AFFECT OF A VIBRATORY ALERT ON A VIBRATION-SENSITIVE SENSOR

FIELD OF THE INVENTION

The present invention relates to implantable medical devices (IMDs), and more particularly to implantable medical devices equipped with both a vibratory alert and a vibration-sensitive sensor.

BACKGROUND

A wide range of implantable medical devices (IMDS) are available for surgical implantation into humans or animals. Some common examples of such IMDs include the cardiac pacemaker, the implantable cardioverter defibrillator (ICD), and the implantable drug pump. Other examples include devices for stimulating or sensing portions of the brain, spinal cord, muscles, bones, nerves, glands, or other body organs/tissues.

Many of such IMDs incorporate sophisticated diagnostic capabilities to monitor an integrity of the IMD and/or patient conditions. For a variety of reasons, it may be appropriate to alert the patient when conditions require an immediate response from the patient, such as seeking medical attention, adjusting a medication dosage, etc. While many types of such alerts have been used in prior art IMDs, the most commonly implemented alert is an audible alert.

Unfortunately, such audible alerts have proven problematic in clinical practice due to false positives. For example, a patient may think that they heard the audible alert when, in fact, they heard a similar environmental sound, such as a cash register, smoke detector, etc. Such false positives are further exacerbated by environmental noise, impaired hearing capacity by the patient, etc. Similarly, false negatives may also be problematic in situations where the patient does not hear the alert, etc.

To address these issues, various prior art IMDs have incorporated a vibratory alert. Such vibratory alerts do not depend on a patient's auditory acuity, nor are they likely to be mistaken for something else. One concern with such vibratory alerts, however, involves the potential affect they may have on vibration-sensitive sensors (e.g. accelerometers, etc.). Specifically, a potential exists for a vibration of the vibratory alert to trigger a response by the vibration-sensitive sensor, thereby resulting in an undesired IMD rate response, etc.

For example, it is possible that a vibratory alert, when activated to generate sufficient vibration to make detection by the patient likely, may generate a level of vibration sufficient to affect a vibration-sensitive sensor. Thus, the vibration-sensitive sensor may interpret such vibration as increased physical activity. Under such circumstances, an IMD rate response algorithm may respond by inappropriately increasing the associated pacing rate.

While this is unlikely to cause direct harm to the patient, it may result in some degree of patient discomfort. For instance, the patient may experience a sensation of palpitations, racing heart, etc. More importantly, such interaction between the vibratory alert and the vibrations-sensitive sensor is contrary to the goal of matching the pacing rate to physiologic demand.

There is thus a need for overcoming these and/or other problems associated with the prior art.

SUMMARY

An implantable medical device (IMD) and associated method are provided including a vibratory alert and a vibration-sensitive sensor. Further included is a circuit in communication with the vibratory alert and the vibration-sensitive sensor. Such circuit is adapted for at least reducing an affect of the vibratory alert on the vibration-sensitive sensor. Thus, in some embodiments, any detrimental result involving a vibration of the vibratory alert triggering a response by the vibration-sensitive sensor may be avoided.

DETAILED DESCRIPTION

Figure 1:
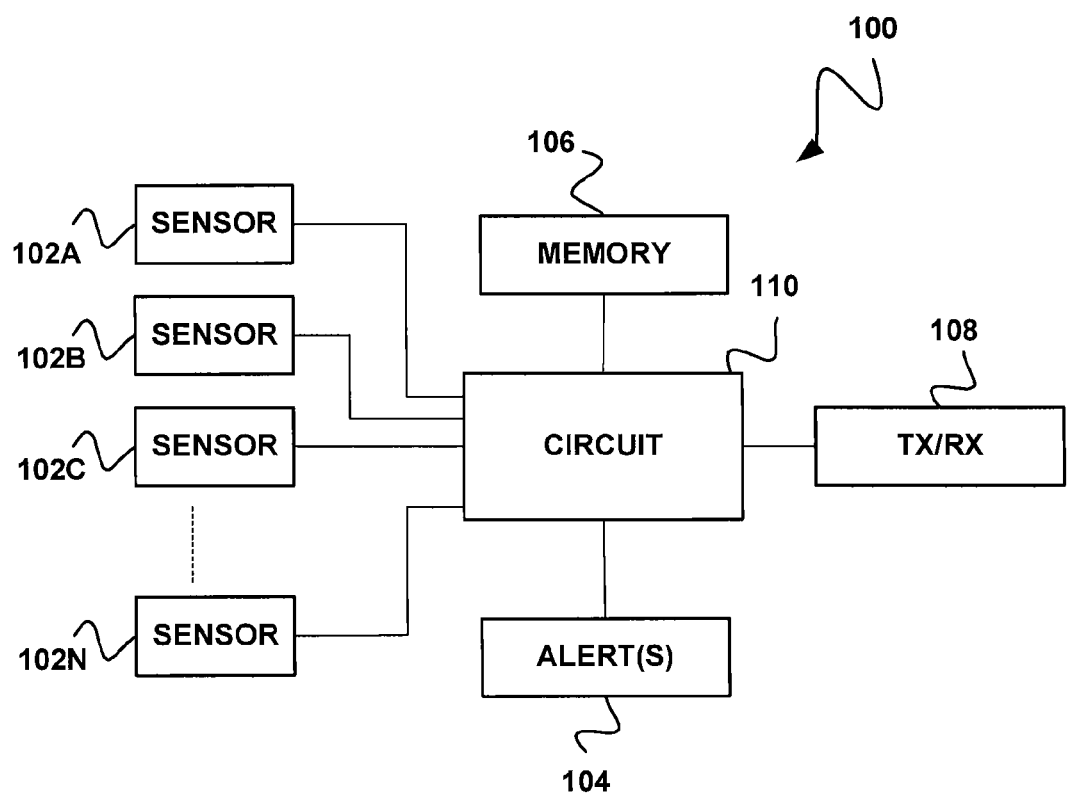
FIG. 1 illustrates an implantable medical device (IMD), in accordance with one embodiment.

FIG. 1 illustrates an implantable medical device (IMD) 100, in accordance with one embodiment. In various embodiments, the IMD 100 may include a cardiac pacemaker, an implantable cardioverter defibrillator (ICD), an implantable drug pump, a device for stimulating and/or sensing portions of the brain, spinal cord, muscles, bones, nerves, glands, and/or any other body organs/tissues, etc. To this end, in the context of the present description, the IMD 100 refers to any device capable of being implanted in a human patient or animal for medical purposes.

As shown, the IMD 100 includes a circuit 110 in communication with a plurality of peripheral components. In one embodiment, the circuit 110 may include a low-power microprocessor. In other embodiments, the circuit 110 may include a microcontroller, an embedded system, a programmable logic device such as a field-programmable logic array, a combinatorial implementation of a state machine, and/or any other type of circuitry.

The aforementioned peripheral components are shown to include a plurality of sensors 102A, 102B, 102C, and 102N (hereinafter "102A-N"), memory 106, a transceiver 108, and one or more alerts 104. While the various peripheral components are shown in FIG. 1 to be discrete components, it should be understood that one or more of such components may be integrated in a single unillustrated IMD housing.

In one embodiment, the transceiver 108 may include an integrated radio frequency telemetry unit. Other embodiments of the transceiver 108 are possible, including acoustic, optic, electrostatic, and magnetic-type transceivers. In yet another embodiment, a receiver component of the transceiver 108 may simply take the form of a reed switch capable of sensing the presence of a strong magnet, so that the IMD can be turned on and off externally, but lacks post-manufacturing programmability. In still other embodiments, the transceiver 108 might not be included, so that the IMD lacks the ability to receive or transmit information.

The alert 104 may include a vibratory alert capable of vibrating when activated. In use, the alert 104 may serve any desired purpose including, but not limited to alerting the patient when conditions require a response, such as contacting a physician, seeking immediate emergency medical attention, adjusting pharmacologic regimens, ceasing exercise or other activities, seeking technical assistance to remedy any deficiency in the performance or integrity of the IMD 100, etc. For example, the alert 104 may be triggered in response to a detection of issues directly related to the performance or integrity of the IMD 100 (e.g. lead fractures, insulation problems, battery depletion, software malfunctions, etc.). In addition, the alert 104 may be triggered in response to clinical conditions that can be detected by the IMD 100 (e.g. a presence of an otherwise imperceptible rhythm disorder, potentially significant levels of ischemia, even non-cardiac conditions unrelated to the primary purpose of the IMD such as glycemic levels, etc.).

In one optional embodiment, the vibratory alert 104 may include a motor that, when activated, rotates an eccentric weight for providing the associated vibration. Of course, however, the vibratory alert 104 may include any other mechanism (e.g. piezoelectric device, etc.) capable of providing a vibration when activated. While a single vibratory alert 104 is discussed in the context of the present embodiment, additional alerts (e.g. acoustic, optic, thermal, electrical stimulation-type alerts, etc.) may also be provided for alerting the patient in other ways.

At least one of the sensors 102A-N (e.g. sensor 102A, for example) includes a vibration-sensitive sensor 102A. In use, in accordance with one embodiment involving a pacemaker-type IMD 100, for example, input from the sensors 102A-N may be used in conjunction with a rate adjustment algorithm for determining a rate at which the IMD 100 paces a heart of a patient. In such embodiment, the vibration-sensitive sensor 102A may include an accelerometer adapted to detect motion indicative of movement of the patient which may, in turn, be used as a surrogate indicator of exercise that requires adjustment of a pacing rate to match a current physiologic demand. Thus, such vibration-sensitive sensor 102A may optionally be used to control the pacing rate of the IMD 100. While an accelerometer is set forth above as an example of a vibration-sensitive sensor 102A, it should be noted that the vibration-sensitive sensor 102A may include any sensor (e.g. microphone-type transducer, etc.) capable of being affected by (e.g. sensing, etc.) vibration.

In various embodiments, at least one of the sensors 102A-N (e.g. sensor 102B, for example) may include a vibration-independent sensor 102B. For example, such vibration-independent sensor 102B may include a respiration sensor, oxygen saturation sensor, pH sensor, temperature sensor, etc. In the context of the present description, the vibration-independent sensor 102B may include any sensor that is at least substantially unaffected by vibration. While multiple sensors are described herein, it should be noted that an embodiment is contemplated including a single vibration-sensitive sensor.

In operation, the circuit 110 serves to at least reduce an affect of the vibratory alert 104 on the vibration-sensitive sensor 102A. In one embodiment, the circuit 110 may optionally reduce any affect to the point that such affect of the vibratory alert 104 on the vibration-sensitive sensor 102A is eliminated completely. To this end, any detrimental result involving a vibration of the vibratory alert 104 triggering a response by the vibration-sensitive sensor 102A may be avoided.

To accomplish this in accordance with one embodiment, any affect of the vibratory alert 104 on the vibration-sensitive sensor 102A may be reduced by disabling the vibration-sensitive sensor 102A. In other embodiments, however, any affect may be reduced by at least partially disregarding (e.g. ignoring, etc.) the vibration-sensitive sensor 102A. Additional information regarding these optional embodiments will be set forth hereinafter in greater detail during reference to subsequent figures. However, it should be strongly noted that the foregoing affect may be reduced in any desired manner that results in the aforementioned reduction.

More illustrative information will now be set forth regarding various optional architectures and features with which the foregoing technique may or may not be implemented, per the desires of the user. It should be strongly noted that the following information is set forth for illustrative purposes and should not be construed as limiting in any manner. Any of the following features may be optionally incorporated with or without the exclusion of other features described.

Figure 2:
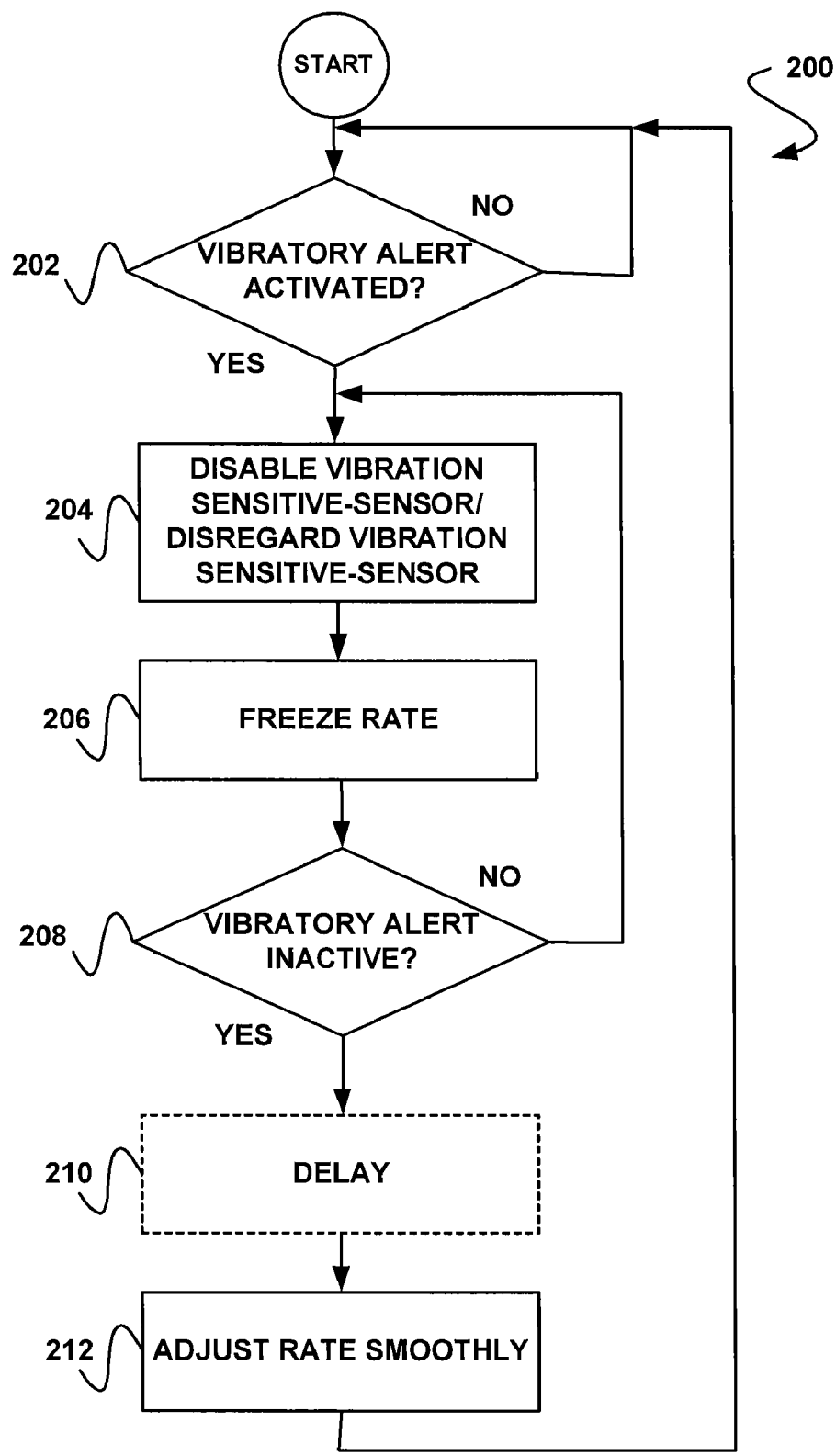
FIG. 2 illustrates a method for reducing an affect of a vibratory alert on a vibration-sensitive sensor, in accordance with another embodiment.

FIG. 2 illustrates a method 200 for reducing an affect of a vibratory alert on a vibration-sensitive sensor, in accordance with another embodiment. As will be set forth below, the method 200 may be carried out in the context of the IMD 100 of FIG. 1 and, in particular, the aforementioned pacemaker. Additionally, the method 200 may be performed under the control of the circuit 100. Of course, it should be noted that the method 200 may be used in any desired environment with any desired IMD. Further, the definitions provided above may equally apply to the present description.

As shown, the method 200 begins upon a vibratory alert (e.g. see, for example, the alert 104 of FIG. 1, etc.) being activated. See decision 202. Such decision 202 may be made by monitoring and detecting a signal that activates the vibratory alert or even receiving a signal from the alert indicating such activation.

Thereafter, in operation 204, any affect that the vibratory alert may have on a vibration-sensitive sensor (e.g. see, for example, the sensor 102A of FIG. 1, etc.) may be reduced by disabling the vibration-sensitive sensor. This may be accomplished, for example, by disconnecting the vibration-sensitive sensor from the circuit during the time that the vibratory alert is activated. Thus, the rate adjustment algorithm remains unaware of any motion detected by the vibration-sensitive sensor in response to the vibratory alert. In other embodiments, the vibration-sensitive sensor might be simply disregarded (e.g. ignored, etc.), at least in part.

In some situations, operation 204 may be complicated by the fact that the vibratory alert could be triggered during a period of exercise which has appropriately resulted in an elevated pacing rate. If the vibration-sensitive sensor were abruptly disabled, disregarded, etc. during this period of exercise, the pacing rate may inappropriately fall, even though the physiologic demands of exercise may still require an elevated pacing rate.

To address this possible concern, a rate at which the pacemaker operates may be controlled to remain substantially constant (e.g. frozen, etc.) in response to the activation of the vibratory alert. See operation 206. For example, the rate at which the pacemaker is operating just prior to the activation of the vibratory alert may be frozen during and after the activation of such alert.

While operation 206 may admittedly preclude any adjustment of the rate in response to any increases or decreases in activity, such level of activity would most likely remain relatively constant during the brief period in which the vibratory alert is activated. Even if some variation in the activity level were to occur during this period, the lack of rate adjustment would not likely be clinically significant, since the magnitude of appropriate rate adjustment during the brief duration of sensor disablement, etc. would probably be small. Of course, while the freeze operation 206 is set forth above, an adjustable rate of some sort is also contemplated during such period, in the context of other alternate embodiments which will be described later.

Operations 204 and 206 continue until it is determined that the vibratory alert is inactive, per decision 208. It should be pointed out that it is possible that some "ringing" associated with the vibratory alert may still exist after the vibration ceases. Further, a smoothing behavior of the rate adjustment algorithm (to be described hereinafter) may also continue to impact operation after the vibration ceases.

Since such considerations may continue to affect the vibration-sensitive sensor for a short period of time after the vibratory alert ceases operation, the rate at which the pacemaker is operating may be held to be substantially constant for a predetermined amount of time (e.g. a delay, etc.) in response to such inactive state. See operation 210. In various embodiments, such amount of time may range from a fraction of a second to a few seconds. Such feature may ensure that the aforementioned ringing, etc. does not affect the vibration-sensitive sensor for such period of time.

In further response to the inactive state of the vibratory alert after operation 210, the rate at which the pacemaker operates may be gradually adjusted, to avoid any sudden rate change. See operation 212. Of course, such gradual adjustment may include, but is not limited to a step function, graduated function, etc. Thus, once the vibratory alert is inactive, the algorithm by which the vibration-sensitive sensor input drives a pacing rate may serve to "smooth" the rate adjustment. To this end, any change due to activity level adjustments that occurred while the vibratory alert was activated may be phased-in in small steps, etc. which will unlikely be perceptible to the patient.

In yet another potential embodiment which may serve as an alternative to the method 200 of FIG. 2, the vibration-sensitive sensor input may continue to be used by the rate adjusting algorithm after vibratory alert activation, in lieu of operations 204-206. However, the algorithm may adjust the rate more slowly in response to changes in sensor input. Thus, any brief excursions caused by the vibratory alert may be smoothed, resulting in very little change in rate. By this design, however, such embodiment may also result in a slow response to true changes in activity.

While such slow response may be acceptable in some embodiments, it may not be desirable in others, especially since patients with IMDs often do not have the capacity to do more than very brief exercise. In such cases, brief but clinically significant periods of exercise, such as walking from one room to the next, may not necessarily result in appropriate timely adjustments in rate.

As mentioned earlier, in another possible embodiment, the vibration-sensitive sensor may coexist with at least one vibration-independent sensor. In use, the vibration-sensitive sensor may exhibit an advantage of providing an immediate response to patient activity. On the other hand, such sensor input may not be proportional to an actual physiologic demand of the patient.

To compensate for such drawback, the vibration-independent sensor may be incorporated, since such type of sensor is typically more proportional and/or directly physiologic in nature. Of course, however, vibration-independent sensors may exhibit a lag between an onset of exercise and an ability to detect a change at the sensor. As yet another option, a first sensor may be used as a primary determinant of rate response, with a second sensor being used to verify an input from the primary sensor.

Thus, in such multi-sensor embodiments, the rate response algorithm may be designed in such a way that different sensors are used during different phases of rate response. In still additional embodiments, the sensor inputs may be blended into a rate adjustment algorithm that uses the input from more than one sensor to determine an appropriate rate, giving proportional weighting to the input of the various sensors. As an option, such weighting may be constant, or each of the sensors may be weighted more or less heavily during various phases.

For example, at the onset of exercise, the vibration-sensitive sensor may be weighted more heavily than a vibration-independent oxygen sensor in order to provide a quicker rate response suitable for short-term demand, while the oxygen sensor may be more heavily weighted later in a sustained exercise period to provide better proportionality of response. Similar to the previous embodiments, the current multi-sensor embodiment is also vulnerable to affects of a vibratory alert on the vibration-sensitive sensor. Thus, a technique will now be described for reducing an affect of such a vibratory alert on the vibration-sensitive sensor in the current weighted multi-sensor environment.

Figure 3:
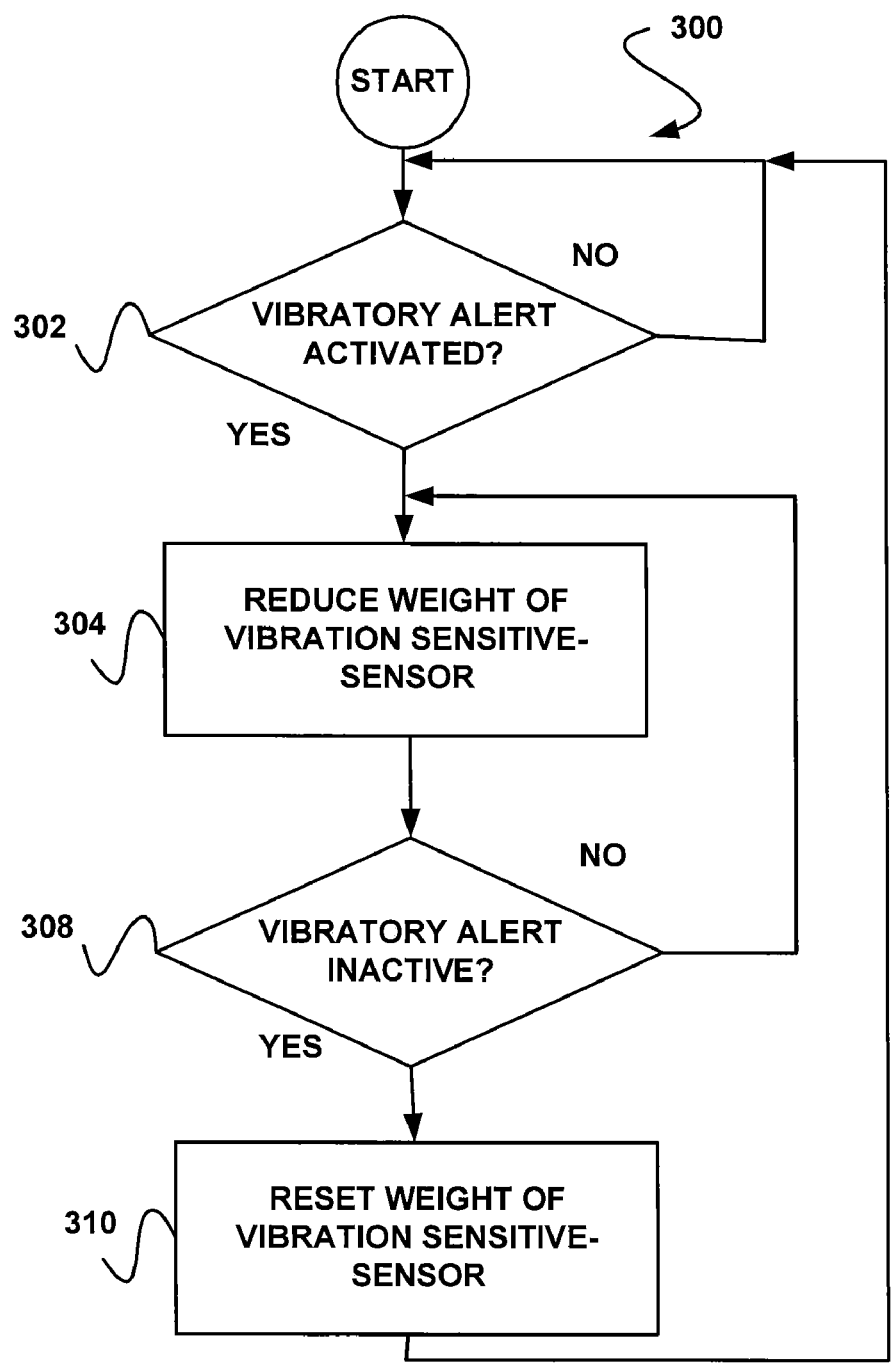
FIG. 3 illustrates a method for reducing an affect of a vibratory alert on a vibration-sensitive sensor in a multi-sensor environment, in accordance with yet another embodiment.

FIG. 3 illustrates a method 300 for reducing an affect of a vibratory alert on a vibration-sensitive sensor in a multi-sensor environment, in accordance with another embodiment. As an option, the method 300 may be carried out in the context of the IMD 100 of FIG. 1 and may or may not incorporate any of the features described in conjunction with the method 200 of FIG. 2. Of course, it should be noted that the method 300 may be used in any desired environment. Again, the definitions provided above may equally apply to the present description.

As mentioned previously, in some embodiments, a vibration-sensitive sensor may coexist with a vibration-independent sensor, and inputs of the vibration-independent sensor and the vibration-sensitive sensor may each be assigned different weights. In such embodiment, an affect of the vibratory alert on a vibration-sensitive sensor may be reduced by reducing a weight assigned to the vibration-sensitive sensor, in response to an activation of the vibratory alert. See operations 302-304. Of course, such reduction may be reset after the vibratory alert ceases, per operations 308-310. While not shown, it should be further noted that such resetting may be delayed, similar to the method 200 of FIG. 2.

Thus, the method 300 of FIG. 3 reduces a dependence of the weighted rate adjustment algorithm on the vibration-sensitive sensor during a period when it is vulnerable to interaction with the vibratory alert. An example of such operation will now be set forth during the description of FIGS. 4-5.

Figure 4:
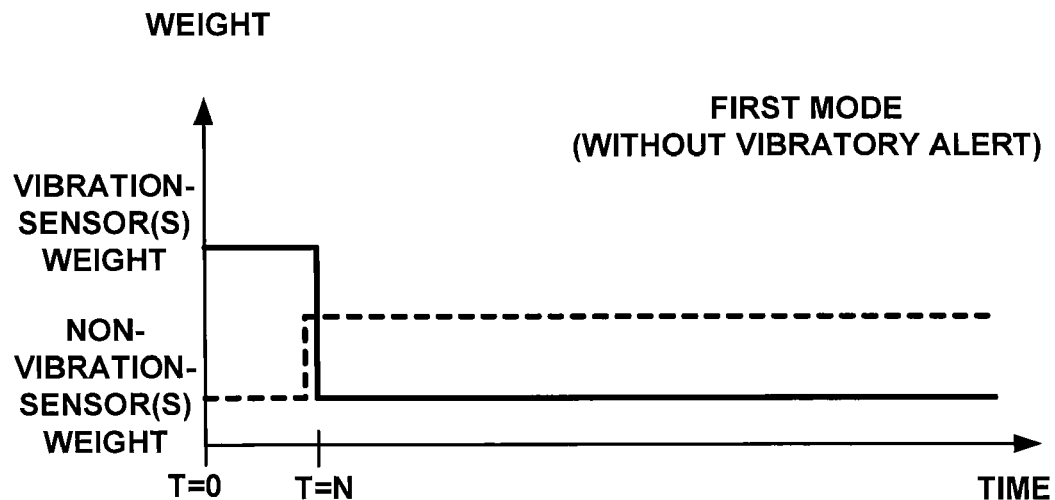
FIG. 4 shows a graph illustrating a weighting scheme that may be used when a vibratory alert is inactive, in accordance with one embodiment.

FIG. 4 shows a graph 400 illustrating a weighting scheme that may be used when a vibratory alert is inactive, in accordance with one embodiment. In the context of the present figure, time=0 indicates a start of physical activity. As shown, a vibration-sensitive sensor may be used during a first phase (e.g. time=0–N) to optimally detect such onset of physical activity.

Thereafter, primary control of the rate response may be switched to a more physiologically-proportional, vibration-independent sensor once such sensor reaches a certain level (which, in FIG. 4, occurs at time=N). While an embodiment is contemplated where dependence on the respective sensors is completely "on" or "off," FIG. 4 shows a technique whereby the various sensor input may be variably weighted in the appropriate manner.

Figure 5:
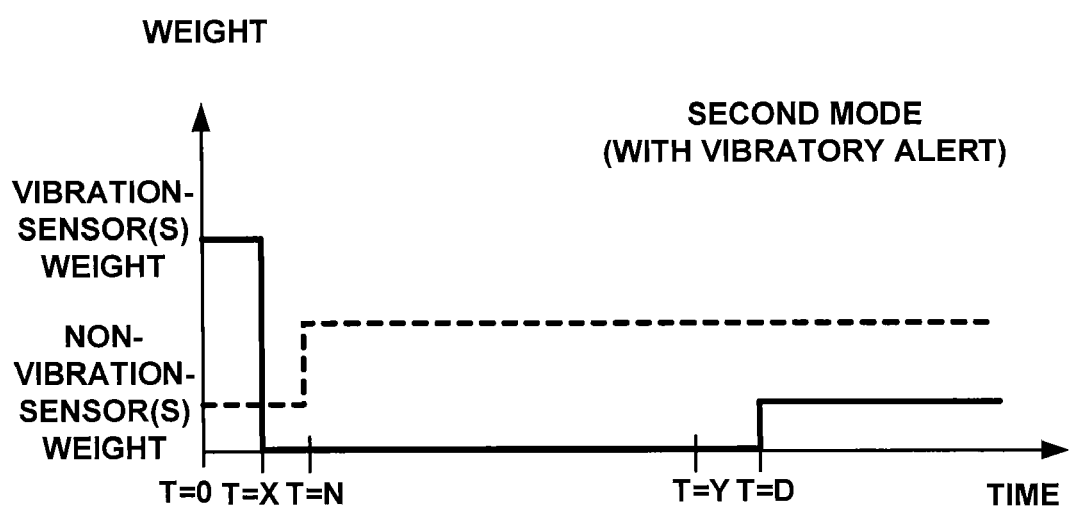
FIG. 5 shows a graph illustrating a weighting scheme that may be used when a vibratory alert is activated, in accordance with one embodiment.

FIG. 5 shows a graph 500 illustrating a weighting scheme that may be used when a vibratory alert is activated, in accordance with one embodiment. In the context of the present figure, the vibratory alert is activated between time=X–Y. As shown, during such time, the weighting assigned to the vibration-sensitive sensor may be reduced (possibly to zero).

As mentioned previously in the context of FIG. 2, reincorporation of the vibration-sensitive sensor input after the vibratory alert is no longer active may occur after a predetermined delay. See operation 210 of FIG. 2. Such delay is reflected in FIG. 5 between time=Y–D, after which the weighting is shown to revert back to that shown in FIG. 4.

Of course, the reduction in weight shown in FIG. 5 is set forth for illustrative purposes only and should not be construed as limiting in any manner. For example, the reduction may also vary as a function of input of other sensors, the reduction may result in a greater-than-zero weighting, the weights of different sensors may or may not overlap, etc. Further, the time period reflected by time=X–Y may be of any desired duration and may occur at any time in relation to physical activity/sensor input.

By this design, the vibration-sensitive sensor may be disabled, ignored, weighted differently, etc. during a period of time that the vibratory alert is functioning, in order to prevent the vibration-sensitive sensor of the IMD from being affected by such alert. Thus, in the context of a pacemaker-type IMD, the pacing rate may be maintained at a current level for the period of time during which the vibration-sensitive sensor is disabled, ignored, weighted differently, etc. To this end, any unwanted and/or inappropriate interaction between the vibratory alert and the vibration-sensitive sensor that controls the pacing rate in the IMD may be avoided.

The foregoing description has described only a few of the many possible implementations of the present invention. For this reason, this detailed description is intended by way of illustration, and not by way of limitations. Variations and modifications of the embodiments disclosed herein may be made based on the description set forth herein, without departing from the scope and spirit of the invention.

It is only the following claims, including all equivalents, that are intended to define the scope of this invention. Moreover, the embodiments described above are specifically contemplated to be used alone as well as in various combinations. Accordingly, other embodiments, variations, and improvements not described herein are not necessarily excluded from the scope of the invention.

What is claimed is:

1. A device: wherein the device is an implantable medical device comprising:
    a vibratory alert;
    a vibration-sensitive sensor; and
    a circuit in communication with the vibratory alert and the vibration-sensitive sensor, the circuit for at least reducing an affect of the vibratory alert on the vibration-sensitive sensor during a period of time that the vibratory alert is active.

2. The implantable medical device of claim 1, wherein the vibration-sensitive sensor includes an accelerometer.

3. The implantable medical device of claim 1, wherein the circuit eliminates the affect of the vibratory alert on the vibration-sensitive sensor.

4. The implantable medical device of claim 1, wherein the affect of the vibratory alert on the vibration-sensitive sensor is reduced by disabling the vibration-sensitive sensor.

5. The implantable medical device of claim 1, wherein the affect of the vibratory alert on the vibration-sensitive sensor is reduced by disregarding the vibration-sensitive sensor.

6. The implantable medical device of claim 1, wherein the implantable medical device includes a pacemaker.

7. The implantable medical device of claim 6, wherein a rate at which the pacemaker operates remains substantially constant in response to activation of the vibratory alert.

8. The implantable medical device of claim 7, wherein the rate at which the pacemaker operates remains substantially constant for a predetermined amount of time in response to the vibratory alert becoming inactive.

9. The implantable medical device of claim 6, wherein a rate at which the pacemaker operates is gradually adjusted in response to the vibratory alert becoming inactive.

10. The implantable medical device of claim 1, and further comprising at least one vibration-independent sensor in communication with the circuit, where inputs of the vibration-independent sensor and the vibration-sensitive sensor each are assigned different weights.

11. The implantable medical device of claim 10, wherein the affect of the vibratory alert on the vibration-sensitive sensor is reduced by reducing a weight assigned to the vibration-sensitive sensor in response to an activation of the vibratory alert.

12. A method, comprising:
    activating a vibratory alert of an implantable medical device; and
    in response to the activation of the vibratory alert, at least reducing an affect of the vibratory alert on a vibration-sensitive sensor of the implantable medical device during a period of time that the vibratory alert is active.

13. The method of claim 12, wherein the vibration-sensitive sensor includes an accelerometer.

14. The method of claim 12, wherein the circuit eliminates the affect of the vibratory alert on the vibration-sensitive sensor.

15. The method of claim 12, wherein the affect of the vibratory alert on the vibration-sensitive sensor is reduced by disabling the vibration-sensitive sensor.

16. The method of claim 12, wherein the affect of the vibratory alert on the vibration-sensitive sensor is reduced by disregarding the vibration-sensitive sensor.

17. The method of claim 12, wherein the implantable medical device includes a pacemaker.

18. The method of claim 17, wherein a rate at which the pacemaker operates remains substantially constant in response to an activation of the vibratory alert.

19. The method of claim 18, wherein the rate at which the pacemaker operates remains substantially constant for a predetermined amount of time in response to the vibratory alert becoming inactive.

20. The method of claim 17, wherein a rate at which the pacemaker operates is gradually adjusted in response to the vibratory alert becoming inactive.

21. The method of claim 12, wherein the implantable medical device includes at least one vibration-independent sensor in communication with the circuit, where inputs of the vibration-independent sensor and the vibration-sensitive sensor each are assigned different weights.

22. The method of claim 21, wherein the affect of the vibratory alert on the vibration-sensitive sensor is reduced by reducing a weight assigned to the vibration-sensitive sensor in response to an activation of the vibratory alert.

23. A subsystem comprising a vibration sensitive sensor: a circuit in communication with the vibration sensitive sensor, a circuit for at least reducing an affect of a vibratory alert of an implantable medical device on the vibration-sensitive sensor of the implantable medical device during a period of time that the vibratory alert is active.

24. The subsystem of claim 23, wherein the vibration-sensitive sensor includes an accelerometer.

25. The subsystem of claim 23, wherein the circuit eliminates the affect of the vibratory alert on the vibration-sensitive sensor.

26. The subsystem of claim 23, wherein the subsystem is a component of a pacemaker.

* * * * *